United States Patent
Dyballa et al.

(10) Patent No.: US 9,610,574 B2
(45) Date of Patent: Apr. 4, 2017

(54) SUPPORTED COMPOSITION AND THE USE THEREOF IN METHODS FOR THE HYDROFORMYLATION OF UNSATURATED COMPOUNDS

(71) Applicant: EVONIK DEGUSSA GMBH, Essen (DE)

(72) Inventors: Katrin Marie Dyballa, Recklinghausen (DE); Hanna Hahn, Duisburg-Baerl (DE); Robert Franke, Marl (DE); Dirk Fridag, Haltern am See (DE); Marc Becker, Dortmund (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 14/914,430

(22) PCT Filed: Aug. 8, 2014

(86) PCT No.: PCT/EP2014/067061
§ 371 (c)(1),
(2) Date: Feb. 25, 2016

(87) PCT Pub. No.: WO2015/028281
PCT Pub. Date: Mar. 5, 2015

(65) Prior Publication Data
US 2016/0200655 A1 Jul. 14, 2016

(30) Foreign Application Priority Data
Aug. 28, 2013 (DE) .................. 10 2013 217 174

(51) Int. Cl.
C07C 45/50 (2006.01)
B01J 31/00 (2006.01)
B01J 8/00 (2006.01)
B01J 31/18 (2006.01)
B01J 8/02 (2006.01)
B01J 31/16 (2006.01)

(52) U.S. Cl.
CPC ............ B01J 31/185 (2013.01); B01J 8/02 (2013.01); B01J 31/1616 (2013.01); C07C 45/50 (2013.01); B01J 2231/321 (2013.01); B01J 2531/822 (2013.01); Y02P 20/588 (2015.11)

(58) Field of Classification Search
CPC ............ C07C 45/50; B01J 31/00; B01J 8/00
USPC .......................................... 568/454; 502/166
See application file for complete search history.

(56) References Cited

U.S. PATENT DOCUMENTS

| 4,769,498 A | 9/1988 | Billig et al. |
| 4,789,753 A | 12/1988 | Billig et al. |
| 5,723,641 A | 3/1998 | Tam et al. |
| 5,767,321 A | 6/1998 | Billig et al. |
| 5,962,744 A | 10/1999 | Ojima et al. |
| 2011/0071321 A1 | 3/2011 | Kreidler et al. |
| 2012/0190894 A1 | 7/2012 | Wegman |
| 2013/0158282 A1 | 6/2013 | Christiansen et al. |
| 2013/0289313 A1 | 10/2013 | Franke et al. |
| 2015/0224488 A1 | 8/2015 | Fridag et al. |

FOREIGN PATENT DOCUMENTS

| DE | 102006058682 A1 | 6/2008 |
| DE | 102008002188 A1 | 12/2009 |
| DE | 102010041821 A1 | 4/2012 |
| EP | 1008581 A1 | 6/2000 |
| WO | 2014/056736 A1 | 4/2014 |
| WO | 2014/170392 A1 | 10/2014 |
| WO | 2015/028284 A1 | 3/2015 |
| WO | 2015/071266 A1 | 5/2015 |
| WO | 2015/086634 A1 | 6/2015 |

OTHER PUBLICATIONS

International Search Report for PCT/EP2014/067061, dated Jan. 13, 2015 in English and German Language.
Armarego, Wilfred L.F., et al. Purification of Laboratory Chemicals, Butterworth Heinemann (Elsevier), 6th edition, Oxford 2009 (index and chapter abstracts provided).
Harris, Robin K. et al. NMR Nomenclature, Nuclear Spin Properties and Conventions for Chemical Shifts. Pure Appl. Chem., 2001, 73, pp. 1795-1818.
Harris, Robin K. et al, Further Conventions for NMR Shielding and Chemical Shifts. Pure Appl. Chem., 2008, 80, pp. 59-84.
Written Opinion of the International Searching Authority for PCT/EP2014/0607061 dated Mar. 5,2015 (15 pages—German with English Translation).
International Preliminary Report on Patentability for PCT/EP2014/0607061 dated Mar. 1, 2016 (17 pages—German with English Translation).

Primary Examiner — Sikarl Witherspoon
(74) Attorney, Agent, or Firm — Smith, Gambrell & Russell, LLP (57) ABSTRACT

The present invention relates to a composition comprising: a) at least one support material; b) at least one metal selected from transition group VIII of the Periodic Table of the Elements and c) at least one compound of the formula (I) R'-A-R" (I), where A, R' and R" are each an organic radical, where R' and R" have the structural element —O—P(—O—)$_2$ with trivalent P and are bonded covalently to the A radical via the latter, with the proviso that R'≠R", to a process for producing such a composition, to the use of the composition and to a process and an apparatus for hydroformylation in which the composition is used.

10 Claims, 2 Drawing Sheets

SUPPORTED COMPOSITION AND THE USE THEREOF IN METHODS FOR THE HYDROFORMYLATION OF UNSATURATED COMPOUNDS

The present invention is directed to a composition comprising: a) at least one support material; b) at least one metal selected from transition group VIII of the Periodic Table of the Elements and c) at least one compound of the formula (I) R'-A-R" (I) where A, R' and R" are each an organic radical, where R' and R" have the structural element —O—P(—O—)$_2$ with trivalent P and are bonded covalently to the A radical via the latter, with the proviso that R'≠R", to a process for producing such a composition, to the use of the composition and to a process and an apparatus for hydroformylation in which the composition is used.

The reactions between olefin compounds, carbon monoxide and hydrogen in the presence of a catalyst to give the aldehydes with one carbon atom more are known as hydroformylation or the oxo process (Scheme 1). The catalysts used in these reactions are frequently compounds of the transition metals of group VIII of the Periodic Table of the Elements, especially rhodium or cobalt catalysts. Known ligands are, for example, compounds from the classes of the phosphines, phosphites and phosphonites, each with trivalent phosphorus P$^{III}$. A good overview of the state of the hydroformylation of olefins can be found in B. CORNILS, W. A. HERRMANN, "Applied Homogeneous Catalysis with Organometallic Compounds", vol. 1 & 2, VCH, Weinheim, New York, 1996 or R. Franke, D. Selent, A. Börner, "Applied Hydroformylation", Chem. Rev., 2012, DOI: 10.1021/cr3001803.

Scheme 1

In conventional homogeneous catalysis, specifically hydroformylation, as described in U.S. Pat. No. 4,769,498 and U.S. Pat. No. 5,723,641, symmetric bisphosphites are preferentially used as ligands. Unsymmetric bisphosphites, when used as ligands in transition metal-catalyzed hydroformylation, have much lower reactivities and lower n-regioselectivity; see Rhodium-catalyzed Hydroformylation, ed. by P. W. N. M. van Leeuwen and C. Claver, Kluwer Academic Publishers 2006, AA Dordrecht, NL, pages 45-46.

As stated by van Leeuwen, the symmetric bisphosphites, as well as higher n/iso selectivities, also have a greater reactivity. Aside from the aim of a high reactivity and n/iso selectivity in relation to the unsaturated compounds to be carbonylated, the stability—specifically the service life—of the catalytically active composition, composed of the metal, ligands and further components having activating action used in each case, with regard to the bisphosphites used as ligands is a constant task in research. This is especially true with regard to olefin-containing mixtures, specifically in the hydroformylation of mixtures of linear olefins.

Aldehydes, especially linear aldehydes such as butyraldehyde, valeraldehyde, hexanal and octanal, are of industrial significance as starting materials for plasticizer alcohols, surfactants and fine chemicals.

In 2008, a total of more than 8 million tonnes of oxo process products were produced by means of hydroformylation.

Catalysts which are generally used in the context of the hydroformylation reaction are especially rhodium and cobalt compounds in the presence of ligands. Catalysts used nowadays in the hydroformylation processes are particularly homogeneously dissolved rhodium-based organometallic catalysts, since it is possible here to choose much milder reaction conditions by contrast with the cobalt-based processes (see: H.-W. Bohnen, B. Cornils, Adv. Catal. 2002, 47, 1).

The hydroformylation of olefins using rhodium-comprising catalyst systems is conducted essentially according to two basic variants.

In one, the Ruhrchemie/Rhone-Poulenc process, the catalyst system consisting of rhodium and a water-soluble ligand, usually alkali metal salts of sulfonated phosphines, is dissolved in an aqueous phase. The reactant-product mixture forms a second liquid phase. There is a flow of synthesis gas and olefin, if it is gaseous, through the two phases which are mixed by stirring. The reactant-product mixture is separated from the catalyst system by phase separation. The organic phase removed is worked up by distillation (see: C. W. Kohlpaintner, R. W. Fischer, B. Cornils, Appl. Catal. A Chem. 2001, 221, 219).

Disadvantages of this process, in addition to the high capital investment and the high operating costs, are that it is only possible to use water-stable ligands and that rhodium losses resulting from leaching are unavoidable. This is particularly problematic since specifically rhodium compounds are comparatively costly noble metal complexes, since rhodium is one of the costliest metals in existence.

In the other variant, the catalyst system comprising rhodium is homogeneously dissolved in an organic phase. Synthesis gas and input olefin are introduced into this phase. The reaction mixture drawn off from the reactor is separated by distillation or membrane separation, for example, into a product-reactant phase and a high boiler phase containing the rhodium-comprising catalyst system. The phase containing the rhodium-comprising catalyst system is recycled into the reactor; the other phase is worked up by distillation (see: K.-D. Wiese, D. Obst, Hydroformylation in: Catalytic Carbonylation Reactions; M. Beller (Ed.), Topics in Organometallic Chemistry 18, Springer, Heidelberg, Germany, 2006, 1).

The hydroformylation gives rise to high boilers. For the most part, these are aldol addition or aldol condensation products of the aldehydes formed. In order that the high boiler concentration in the reactor remains limited, a substream, ideally one in which the high boilers are concentrated, has to be discharged. Rhodium compounds are present in this substream. In order to keep the rhodium losses small, rhodium has to be recovered from this discharge stream. The separation of rhodium from such streams is incomplete and complex. Further rhodium losses occur as a result of rhodium cluster formation. These rhodium clusters separate out on equipment walls and may form alloys with the equipment materials. These amounts of rhodium are no longer catalytically active and, even after the plant has been shut down, can be recovered only in a very complex manner and also only in part.

Since the economic viability of an industrial hydroformylation process is substantially dependent on the specific rhodium consumption because of the exceptionally high cost of rhodium in the last few years, attempts have been made to develop alternative processes which feature lower specific rhodium losses.

The starting point in the development of novel hydroformylation processes was the idea of immobilizing rhodium-containing catalyst systems which were previously in homogeneous form in the reaction mixture. This may be referred to as the heterogenization of a reaction conducted homogeneously in principle—in this case hydroformylation.

In the last few decades, numerous techniques for the immobilization of homogeneous catalysts have been developed, and many of these concepts have been employed for hydroformylation reactions (see: M. Beller, B. Cornils, C. D. Frohning, C. W. Kohlpaintner, *J. Mol. Catal.* 1995, 104, 17).

The heterogenization of the catalyst complexes by immobilization on porous support materials has been studied in detail. Such heterogenization can be achieved, for example, by covalent anchoring of the rhodium complex on the support via spacer ligands (see: V. A. Likholobov, B. L. Moroz, *Hydroformylation on Solid Catalysts in: Handbook of Heterogeneous Catalysis,* 2nd ed.; G. Ertl, H. Knoezinger, F. Schüth, J. Weitkamp (eds.), Wiley-VCH, Weinheim, Germany, 2008, 3663).

Aside from the supported aqueous phase (SAP) concept (see H. Delmas, U. Jaeuregui-Haza, A.-M. Wilhelm, *Supported Aqueous-Phase Catalysis as the Alternative Method in: Multiphase Homogeneous Catalysis*, B. Cornils, W. A. Herrmann, I. T. Horváth, W. Leitner, S. Mecking, H. Olivier-Bourbigou, D. Vogt (Eds.), Wiley-VCH, Weinheim, Germany, 2005), which, however, is unsuitable for hydrolysis-sensitive ligands, the supported liquid phase (SLP) concept is a further concept for heterogenization of homogeneous catalyst complexes. This involves applying a liquid catalyst solution to a porous support material. This concept has already been known for more than 40 years (see: P. Rony, *J. Catal.* 1969, 14, 142; G. J. K. Acres, G. C. Bond, B. J. Cooper, J. A. Dawson, *J. Catal.* 1969, 6, 139). Liquid phases used for the hydroformylation include molten salts, for example triphenylphosphine (TPP). TPP serves here as solvent for the catalyst complex, but also as ligand, and is therefore used in a large excess. A problem with such a great ligand excess in catalyst systems under consideration is the formation of various transition metal complexes which can result in suppression of catalytic activity.

According to the literature, however, purely heterogeneous catalysts suffer from a low hydroformylation activity but feature quite a high hydrogenation activity which is undesirable in this case (see: a) M. E. Davis, E. Rode, D. Taylor, B. E. Hanson, *J. Catal.* 1984, 86, 67; b) S. Naito, M. Tanimoto, *J. Chem. Soc. Chem. Commun.* 1989, 1403; c) G. Srinivas, S. S. C. Chung, *J. Catal.* 1993, 144, 131). Without the presence of a liquid reaction phase in which the organometallic catalyst complex is present in dissolved form, poor regioselectivity is often found.

The most promising development to date is the hydroformylation of olefins to afford aldehydes using what are known as supported ionic liquid phase catalyst systems or SILP catalyst systems for short. These are catalytically active compositions in a polyphasic system consisting of a solid inert porous support material surrounded by an ionic liquid—called the SILP phase—in which the transition metal-containing, especially rhodium-containing, catalyst is present (see: a) A. Riisager, P. Wasserscheid, R. van Hal, R. Fehrmann, *J. Catal.* 2003, 219, 252; b) M. Haumann, K. Dentler, J. Joni, A. Riisager, P. Wasserscheid, *Adv. Synth. Catal.* 2007, 349, 425; c) S. Shylesh, D. Hanna, S. Werner, A. T. Bell, *ACS Catal.* 2012, 2, 487; d) M. Jakuttis, A. Schoenweiz, S. Werner, R. Franke, K.-D. Wiese, M. Haumann, P. Wasserscheid, *Angew. Chem. Int. Ed.* 2011, 50, 4492).

With SILP catalyst systems, it is possible to combine the advantages of homogeneously and heterogeneously catalyzed synthesis reactions. This relates particularly to the product removal and recycling of the catalyst, especially of the transition metals present therein, which is found to be difficult and inconvenient in the case of homogeneously conducted synthesis reactions. Heterogeneously catalyzed synthesis reactions, in contrast, may be limited by heat and mass transfer, which reduces the activity of the solid catalyst system; lower chemo- and stereoselectivities are also observed in heterogeneously catalyzed synthesis reactions.

The use of a highly active and selective catalyst system is not the only important factor for the economic operation of a continuous process for hydroformylation. Particular aspects that play a crucial role are catalyst recycling—associated with the product removal—and ligand stability—not only in view of the high costs of rhodium and ligands, but also of the only partially understood influence of impurities from ligand degradation processes on the activity and product spectrum.

A disadvantage of the SILP process described in this context is the use of the ionic liquid, called IL for short; the long-term toxicity of these ionic liquids is not entirely clear as yet, and it has been found that some possible cations and anions are toxic to the environment. One example is comparatively long alkyl chains, which are toxic to the aquatic environment. Two further problems are that production costs are still too high and that many ionic liquids lack stability to comparatively high temperatures.

An additional factor is that the commercially available ILs, because of their synthesis, may contain traces or even comparatively large amounts of water in most cases. The drying of these ionic liquids is generally very complex and problematic, since it does not succeed in all cases.

The additional introduction of water via the ionic liquid is particularly critical, since it is common knowledge that organophosphorus ligands in hydroformylation are subject to an inherent degradation and deactivation process [P. W. N. M. van Leeuwen, in Rhodium Catalyzed Hydroformylation, P. W. N. M. van Leeuwen, C. Claver (eds.), Kluwer, Dordrecht, 2000].

Side reactions and degradation reactions may, for example, be hydrolysis, alcoholysis, transesterification, Arbuzov rearrangement, P—O bond cleavage and P—C bond cleavage [P. W. N. M. van Leeuwen, in Rhodium Catalyzed Hydroformylation, P. W. N. M. van Leeuwen, C. Claver (eds.), Kluwer, Dordrecht, 2000.; F. Ramirez, S. B. Bhatia, C. P. Smith, Tetrahedron 1967, 23, 2067-2080.; E. Billig, A. G. Abatjoglou, D. R. Bryant, R. E. Murray, J. M. Maher, (Union Carbide Corporation), U.S. Pat. No. 4,789, 753 1988; M. Takai, I. Nakajima, T. Tsukahara, Y. Tanaka, H. Urata, A. Nakanishi, EP 1 008 581 B1 2004.].

The effect of ligand deactivation and degradation is that less active ligand is present in the system, which can have an adverse effect on the performance of the catalyst (conversion, yield, selectivity).

Thus, additional introduction of substances that accelerate this catalyst degradation, for example introduction of water via the IL, should be avoided.

Ligand systems known from the literature for gas phase hydroformylation with SILP systeams include bisphosphites (DE 102010041821), mono- and bisphosphines (Riisager et al., *Catal. Lett.* 2003, 90, 149.; Riisager et al. *J. Catal.* 2003, 219, 452). Bisphosphites are notable for a high long-term stability of 700 h at a reaction temperature of 100° C. For the reasons mentioned above, SILP catalysts without ILs can achieve prolonged service lives of up to 1000 h and n/iso selectivities greater than 95% (Schonweiz et al., Chem. Cat. Chem., 2013, DOI: 10.1002/cctc.201300305). Sulfonated bisphosphines of the xantphos type as SILP catalyst without ILs, compared to systems comprising ILs ([BMIM][$PF_6$]), in a five-hour hydroformylation reactions of propene, show a distinct increase in activity (TOF(L/Rh ratio=2.5)=37.4 $h^{-1}$ without ILs compared to 5.1 $h^{-1}$ with [BMIM][$PF_6$]; or TOF(L/Rh ratio=10.2 without ILs or 10 with [BMIM][$PF_6$])=40.8 $h^{-1}$ without ILs compared to 37.0 $h^{-1}$ with [BMIM][$PF_6$]) with an only slightly lower n/iso selectivity (n/iso selectivity (L/Rh ratio=2.5)=1.7% without ILs compared to 2.0% with [BMIM][$PF_6$]; or TOF(L/Rh ratio=10.2 without ILs or 10 with [BMIM][$PF_6$])=16.9% without ILs compared to 23.3% with [BMIM][$PF_6$]) (Riisager et al., *J. Catal.* 2003, 219, 452). Rh-monophosphines (Riisager et al., *Catal. Lett.* 2003, 90, 149), in propene hydroformylation reactions, as SILP catalysts without ILs, also give a much higher activity (turnover frequency) and comparable n/iso selectivity.

In many industrial streams, internal olefins frequently are also found as well as terminal alkenes. It is therefore important to develop a catalytically active composition suitable not only for the conversion of terminal alkenes but also for conversion in an isomerizing hydroformylation. However, the benzpinacol-type ligands known from the literature are inactive in an isomerizing hydroformylation, as already disclosed by DE 102006058682.

This ligand type is the most stable system to date for a catalytically active composition in the heterogenization of the homogeneous hydroformylation reaction, as already disclosed by DE 102010041821.

In this connection, it is desirable to develop catalytically active compositions which are capable of isomerizing hydroformylation and are much more stable than the prior art to date, i.e. which feature a distinctly prolonged onstream time.

For an industrial scale hydroformylation process, not just the n/iso selectivity >90% but also the service life of a catalyst is of crucial importance. Every catalyst exchange necessitates changeover periods in the production plant in which the production plant is not in operation. Within these periods, no return can be achieved with this production plant.

It was therefore an object of the present invention to provide a catalyst system for hydroformylation, which does not have one or more of the disadvantages of the prior art catalyst systems.

More particularly, it was an object of the present invention to provide a process for hydroformylation which both enables favorable catalyst removal and does not require the addition of further components, and preferably simultaneously has improved catalyst service life compared to the systems described in the prior art.

It has been found that, surprisingly, this object can be achieved by a composition as claimed in claim 1, which includes a catalyst complex on a heterogeneous support, said complex including an unsymmetrically substituted bisphosphite ligand.

The composition of the invention has the advantage that it is possible to dispense with, for example, the addition of an IL as required by an SILP catalyst system. In this way, it is firstly possible to save costs for synthesis of the IL or the procurement thereof; secondly, it is possible to avoid the introduction of catalyst poisons such as water via the IL.

A further advantage of the composition of the invention is the long catalyst service lives, especially in the case of applications of the composition as catalyst in gas phase reactions, since it is possible to dispense with multiple catalyst exchange over the course of a year of operation. Thus, the heterogenization of a homogeneous ligand complex by means of an SILP system of prolonged stability, without addition or without the presence of ionic liquids on porous support materials, leads to service lives of more than 3500 h and to n/iso selectivities averaging more than 90%. This at the same time means simplified product removal and recovery of the catalyst, especially of the transition metals present therein, compared to homogeneous systems since it is possible to use a fixed bed reactor.

A further advantage of the composition of the invention is that it catalyzes not only conversion of terminal alkenes but also conversion in an isomerizing hydroformylation.

The suitability of the catalyst system of the invention for the hydroformylation is especially surprising since unsymmetric bisphosphites, when used as a ligand in transition metal-catalyzed hydroformylation in the liquid phase, generally have much lower reactivities and lower n-regioselectivity than symmetrically substituted bisphosphite ligands; see Rhodium-catalyzed Hydroformylation, ed. by P. W. N. M. van Leeuwen and C. Claver, Kluwer Academic Publishers 2006, AA Dordrecht, NL, pages 45-46. The unsymmetric bisphosphites ligand used in the system claimed does not have the disadvantages described in the prior art. Compared to all heterogenized symmetric bisphosphites mentioned in the prior art, the composition of the invention has by far the best catalyst service life and hence is notable for high stability.

The compositions of the invention and the use thereof are described hereinafter by way of example, without any intention that the invention be restricted to these illustrative embodiments. When ranges, general formulae or compound classes are specified hereinafter, these shall include not just the corresponding ranges or groups of compounds that are explicitly mentioned but also all sub-ranges and sub-groups of compounds which can be obtained by removing individual values (ranges) or compounds. When documents are cited in the context of the present description, the contents thereof, particularly with regard to the subject matter that forms the context in which the document has been cited, are considered in their entirety to form part of the disclosure content of the present invention. Unless stated otherwise, percentages are figures in percent by weight. When average values are reported hereinbelow, the values in question are weight averages, unless stated otherwise. When parameters which have been determined by measurement are reported hereinafter, they have been determined at a temperature of 25° C. and a pressure of 101.325 Pa, unless stated otherwise.

The term "inert" in the context of the present invention is understood to mean the property of substances, components or mixtures of causing no adverse effects or effects contrary to the intended course of the reaction.

It is a feature of the composition of the invention that it comprises:

a) at least one support material which is preferably porous;

b) at least one metal selected from transition group VIII of the Periodic Table of the Elements;

c) at least one compound of the formula (I)

$$R'-A-R''  \quad (I)$$

where A, R' and R" are each an organic radical, where R' and R" have the structural element —O—P(—O—)$_2$ with trivalent P and are bonded covalently to the A radical via the latter, with the proviso that R'≠R".

Support materials used may be any known support materials, preferably porous support materials. Preferably, porous support materials used are those which are inert with respect to the further constituents of the composition and the co-reactants and reaction products of the reactions in which the compositions are used. Preferred support materials are inorganic, preferably oxidic support materials. Suitable support materials are especially oxides of aluminum, silicon, titanium or zirconium or activated carbon or mixtures thereof, which may optionally include further elements. Preferred support materials are, for example, aluminosilicates, zeolitesx $Al_2O_3$ or silicon dioxide. More preferably, the support material includes or consists of silicon dioxide.

The porous support material preferably has the following surface parameters:
i) mean pore diameter within a range from 1 to 423 nm;
ii) pore volume within a range from 0.1 to 2 mL/g;
iii) BET surface area within a range from 10 to 2050 $m^2/g$,
where these values are determined by the Hg method to DIN 66133 and $N_2$ adsorption to DIN 66131 and DIN 66135.

The A, R' and R" radicals in the compound of the formula (I) in the composition of the invention are selected from substituted and unsubstituted 1,1'-biphenyl, 1,1'-binaphthyl and ortho-phenyl radicals, especially from substituted and unsubstituted 1,1'-biphenyl radicals.

More particularly, the compound of the formula (I) in the composition of the invention is selected from a compound of the formula (II):

(II)

where the compound of the formula (II) may have further constituents attributable to impurities in the synthesis of (II), for example unconverted reactant, hydrolysis and oxidation products of (II) or further impurities.

In the composition of the invention, the metal is preferably selected from: cobalt, rhodium, iridium, ruthenium, especially rhodium.

The composition of the invention can be produced in any known manner, by mixing the components. Preferably, the composition of the invention is produced by the process of the invention described hereinafter, or is obtainable thereby.

The process of the invention for producing the composition of the invention features the following steps:

a) initially charging a precursor of at least one compound of a metal from transition group VIII of the Periodic Table of the Elements;

b) contacting at least one compound of a metal from transition group VIII of the Periodic Table of the Elements with a molar excess of at least one organic phosphorus compound of the formula (I) R'-A-R" (I) using an inert solvent;

c) adding at least one porous inert support material to the mixture generated in b);

d) removing the inert solvent to obtain the catalytically active composition;

where, preferably, steps a) to c) are performed in any sequence, and where, preferably, in step a), at least one compound of a metal of transition group VIII can be initially charged in an inert solvent.

The composition of the invention can be used as a catalytically active composition. Preferably, the composition of the invention is used as a catalytically active composition in a process for hydroformylating unsaturated compounds or mixtures thereof.

Accordingly, it is a feature of the process according to the invention for hydroformylating unsaturated compounds that an inventive composition is used as catalyst. Preferably, the process of the invention for hydroformylation of unsaturated compounds or mixtures thereof is conducted in a fixed bed reactor comprising the composition of the invention.

The unsaturated compounds are preferably selected from the $C_2$-$C_4$ olefins and industrial mixtures thereof, as present, for example, as raffinate streams—raffinate I, II or III—in processing and further processing in the petrochemical industry, especially ethene, propene, butenes or mixtures including these compounds.

The present invention further provides an apparatus for hydroformylation of unsaturated compounds which is operated as a fixed bed reactor and is characterized in that it includes a composition of the invention, preferably in or as a fixed bed.

The present invention finally provides a polyphasic reaction mixture including:
1) at least one unsaturated compound;
2) a gas mixture comprising carbon monoxide, hydrogen and
3) aldehydes and conversion products thereof,
in the presence of the composition of the invention.

The present invention is elucidated in detail with reference to the figures FIG. 1 and FIG. 2, without any intention of restricting the invention, the scope of application of which is apparent from the entirety of the description and the claims, to the embodiments specified in the examples.

Non-inventive.

before (and after) variation of the H$_2$/1-butene ratio from 6 to 8 after reaction time 170 h, residence time=48 s (43 s). For better clarity, only every 10th of the measurements obtained was shown compared to the literature (Schonweiz et al., Chem. Cat. Chem., 2013, DOI: 10.1002/cctc.201300305).

Inventive.

The examples listed below illustrate the present invention by way of example, without any intention of restricting the invention, the scope of application of which is apparent from the entirety of the description and the claims, to the embodiments specified in the examples.

EXAMPLES

All the preparations which follow were carried out under protective gas using standard Schlenk techniques. Unless stated otherwise, the solvents were dried over suitable desiccants before use (Purification of Laboratory Chemicals, W. L. F. Armarego (author), Christina Chai (author), Butterworth Heinemann (Elsevier), 6th edition, Oxford 2009).

Chemicals (Acetylacetonato)dicarbonylrhodium—(Rh(acac)(CO)$_2$) in abbreviated form—and dichloromethane (HPLC purity) were used without further purification. Medium-pore silicon dioxide is obtainable commercially as silica gel 100 (0.2-0.5 mm) for column chromatography from Merck KGaA. For production of the catalytically active composition, silicon dioxide was calcined at 450° C. for 24 h and then stored under reduced pressure at 200 Pa for a further 24 h. The silicon dioxide was subsequently stored under an argon atmosphere. The ligand (II) was prepared according to the following reaction scheme:

Abbreviations:
DM water=demineralized water
CPG=core-pulled precision glass
ACN=acetonitrile
acac=acetylacetonate
NEt$_3$=triethylamine All the preparations which follow were carried out under protective gas using standard Schlenk techniques. The solvents were dried over suitable desiccants before use (Purification of Laboratory Chemicals, W. L. F. Armarego (Author), Christina Chai (Author), Butterworth Heinemann (Elsevier), 6th edition, Oxford 2009).

The products were characterized by means of NMR spectroscopy. Chemical shifts (δ) are reported in ppm. The $^{31}$P NMR signals were referenced as follows: SR$_{31P}$=SR$_{1H}$* (BF$_{31P}$/BF$_{1H}$)=SR$_{1H}$*0.4048. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84). By means of $^{31}$P

NMR, the content of the ligand (II) was determined, with characterization of this unsymmetric ligand by two phosphorus signals.

Synthesis of 2,2'-bis(3,5-dimethylphenol) chlorophosphite (6)

(5)

+PCl₃ →

(6)

A 2 L Schlenk with magnetic stirrer, which had been repeatedly evacuated and filled with inert gas, was initially charged with 440 mL of phosphorus trichloride. 120 g of 2,2'-bis(3,5-dimethylphenol) were weighed into a second 1 L Schlenk which had been repeatedly evacuated and filled with inert gas, and 500 mL of dried toluene were added while stirring. The biphenol-toluene suspension was metered into the phosphorus trichloride at 63° C. within 4 h. On completion of the addition, the reaction mixture was stirred overnight at temperature. The next morning, the solution was concentrated while warm (45° C.), and the product was obtained in 96.5% yield (153 g). $^{31}$P NMR: 175.59 (94.8% 2,2'-bis(3,5-dimethylphenol) chlorophosphite), 4.4% various PCl compounds, 0.8% P—H compound.

Synthesis Method for Preparation of the Pure Ligand (II)

(7)

+

(6)

→

(II)

In a 1000 mL Schlenk, under protective gas, 38.75 g (0.121 mol) of 2,2'-bis(3,5-dimethylphenyl) chlorophosphite were dissolved in 150 mL of degassed ACN and heated to 35° C. In a second Schlenk (500 mL), 20.1 g (0.056 mol) of 3,3'-di-tert-butyl-5,5'-dimethoxy-[1,1'-biphenyl]-2,2'-diol were dissolved in 150 mL of degassed ACN, and 40.9 mL of degassed NEt₃ (0.29 mol) were added while stirring. The biphenol/NEt₃ solution was then slowly added dropwise to the chlorophosphite solution. After a further reaction time of 1 h, the reaction solution was stirred at 45° C. overnight.

These solids were suspended in degassed ACN at 75° C. for 1.5 h and removed and washed with warm ACN. Subsequently, the product was suspended in toluene at 35° C. for 1.5 h and washed. The target product (II) was obtained as a white solid (33 g, 66%). $^{31}$P NMR (202.4 MHz, toluene-d₈): 142.5 and 140.9 (100%).

The symmetric bisphosphite ligand (III) was prepared according to DE 102006058682.

(III)

Synthesis gas consists of a mixture having a proportion by volume of 1:1 of hydrogen and carbon monoxide (≥99.97%). The technical C4 mixtures had the compositions specified in table 2:

TABLE 2

| | Composition of C4 mixture A/%[a] Rh(II): 0-2615 h | Composition of C4 mixture B/%[a] Rh(II): 2615-3506 h | Composition of C4 mixture C/%[a] Rh(III): 0-1195 h |
|---|---|---|---|
| 1-butene + isobutene | 24.9 (24.8 + <0.1) | 27 (26.9 + <0.1) | 27.8 (27.8 + <0.1) |
| cis-2-butene | 16 | 16 | 16 |
| trans-2-butene | 33 | 29 | 28 |
| n-butane | 26 | 27.9 | 28 |
| isobutane | <0.1 | <0.1 | <0.1 |

[a]GC area in % (column: Agilent Technologies, length 50 m, internal diameter 0.32 mm, film thickness 0.5 μm, carrier gas helium; detector: FID, vaporizer temperature 473.15 K, split ratio 33.5:1, constant column flow rate of helium 91.6 mL min$^{-1}$, detector temperature 523.15 K, heating ramp: starting temperature 323.15 K, hold time 15 min, heating to 473.15 K at 25 K min$^{-1}$, hold time 40 min, total time per analysis 61 min)

Preparation of the Catalytically Active Composition

All the preparations of the catalytically active composition were effected by means of Schlenk methodology under argon (≥99.99%). 0.40 mmol of Rh(CO)$_2$(acac) was dissolved in about 160 mL of dichloromethane and stirred for 10 min. A ten-fold excess of ligand (II) (molar ligand/rhodium ratio=10) was added to the rhodium precursor solution and stirred for 10 min. Subsequently, the required amount of calcined silicon dioxide, silica gel 100 (mass ratio of rhodium/support material=0.2%), was added. The suspension obtained was stirred for 60 min. Dichloromethane was subsequently drawn off under reduced pressure on a rotary evaporator at 700 hPa and 40° C., and the resulting powder was dried under fine vacuum (40 Pa) for 24 h. Before the catalytically active composition was used, it was stored under an argon atmosphere. The catalytically active composition having the ligand (III) is prepared on the basis of DE 102010041821, explicitly dispensing with the addition of the ILs and, as a further component, of the organic amine.

Catalysis Experiments

All the hydroformylation experiments were conducted in a fixed bed reactor. The dry catalyst material was charged into the tubular reactor and fixed with a piece of glass wool on either side. The overall system was purged with argon at room temperature and then pressurized with the reaction pressure (argon). If no pressure drop was found, the reactor in the argon stream was heated up to reaction temperature. After the respective volume flow rates have been set, synthesis gas (CO and H$_2$; volume=1 to 1, ≥99.97%) is passed through the reactor for 4 hours. The synthesis gas is metered in by means of mass flow regulators (source: Bronkhorst). The reactant metering of the C4 mixture was effected by means of an HPLC pump (source: Knauer). In a mixer filled with glass beads, the reactant gas stream was homogenized before it flowed through the tubular reactor, including the catalyst bed, from the top. The reactor consisted of stainless steel (diameter 12 mm, length 390 mm) and had a grid for positioning of the catalyst material on the outlet side. By means of an internal thermocouple, it was possible to record the temperature in the catalyst bed. The total pressure in the experimental system was regulated by means of an electronic pressure-retaining valve (source: Samson). On the low-pressure side, the product gas stream was divided with the aid of a valve, such that only a small proportion of the total stream was passed to the online gas chromatograph (source: Agilent, model: 6890). The greater proportion was passed directly into a product drum. Through a valve, samples of the product gas stream were injected into the gas chromatograph at regular intervals. The data were evaluated by means of the ChemStation software from Agilent.

Analysis

The product gas composition was analyzed with an online gas chromatograph during the experiment run time. The gas chromatograph was equipped with a dimethylpolysiloxane-coated column (from Agilent Technologies, length 50 m, internal diameter 0.2 mm, film thickness 0.5 μm) and a flame ionization detector (FID). Analysis parameters set: injector temperature 473.15 K, split ratio 33.5:1, constant column flow rate of helium 74 mL min$^{-1}$, detector temperature 523.15 K, heating ramp: starting temperature 323.15 K, hold time 15 min, heating to 473.15 K at 25 K min$^{-1}$, hold time 40 min, total time per analysis 61 min.

Results

Figure 1:
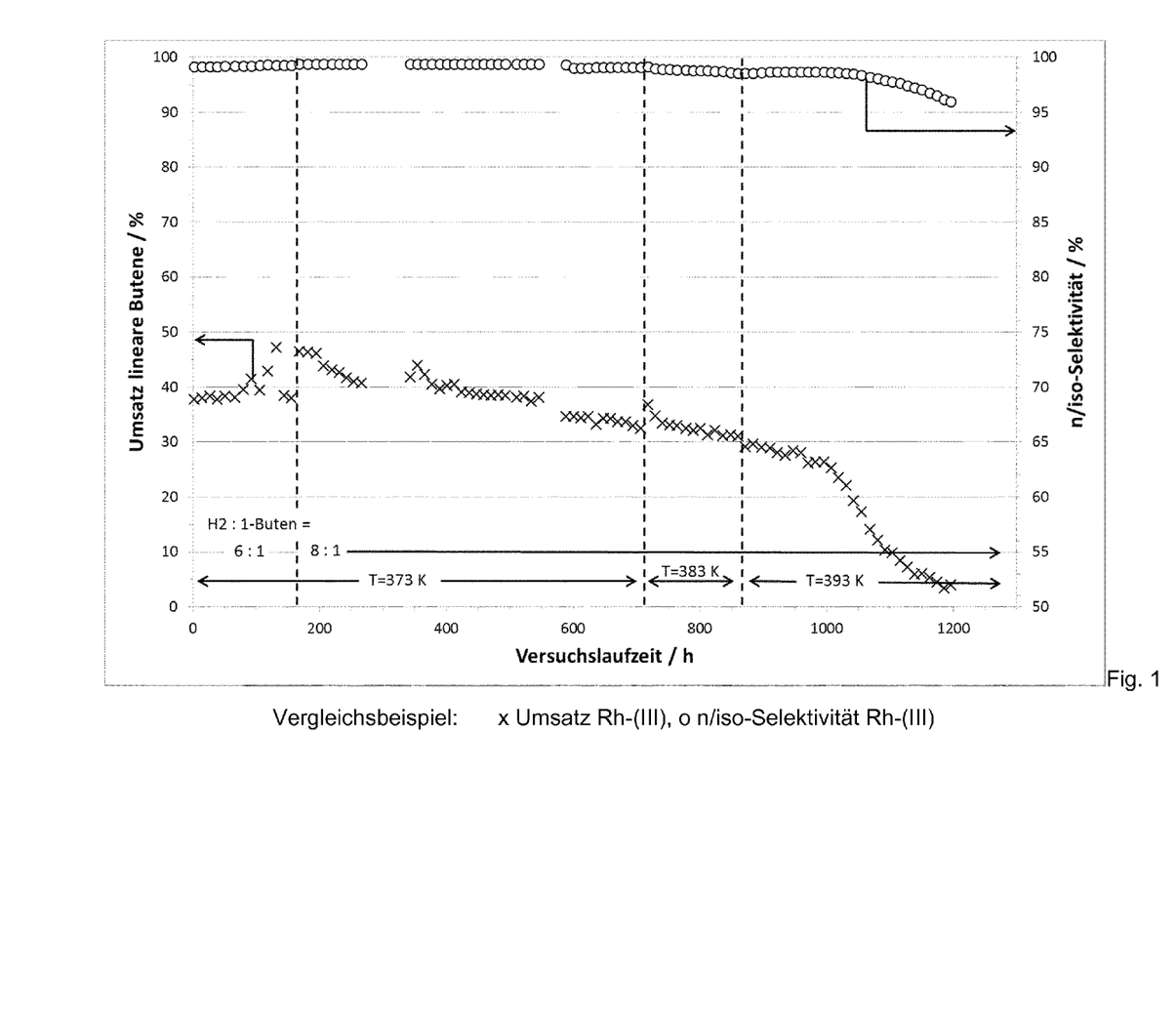
FIG. 1 shows a conversion/time diagram for C4 hydroformylation with Rh(III) catalysts (x) and the n/iso selectivity (○). Parameters: $m_{cat}$=12 g, $m_{Rh}$=0.2% by wt., L/Rh=10, x, ○: T=373.15-393.15 K; p=1 MPa; p(1- and 2-butenes)=0.16 MPa (0.13 MPa); p(butanes)=0.06 MPa (0.05 MPa); p($H_2$)=p(CO)=0.39 MPa (0.41 MPa)

The benzpinacol-based ligand (III) known from the literature, as catalytically active composition Rh(III), in the reaction with technical C4 mixtures (for composition see table 1, column 3), exhibits a very good n/iso selectivity of >90% with a conversion of linear butenes of initially >38% (cf. FIG. 1). After an onstream time of 170 h, with a high H$_2$/1-butene ratio under reaction conditions of 8, the catalytically active Rh(III) composition exhibits a typically high n/iso selectivity of 99.4% for the linear aldehyde n-pentanal. These high selectivity results are comparable with results for pure 1-butene (Schonweiz et al., Chem. Cat. Chem., 2013, DOI: 10.1002/cctc.201300305). After alteration of the H$_2$/1-butene ratio, creeping deactivation takes place over the reaction time in question. Thereafter, a variation of temperature up to a reaction temperature of 120° C. was conducted (cf. FIG. 1). At a temperature of 120° C. and an onstream time of about 1000 h, severe deactivation of the catalyst system takes place within about 200 h. With this drop in conversion, there is likewise a fall in the n/iso selectivity to 96%. One possible explanation for the deactivation may be the formation of water as by-product of the aldol condensation from the aldehydes formed. Ligand (III), being a bisphosphite, has a tendency to alcoholysis inter alia.

Figure 2:
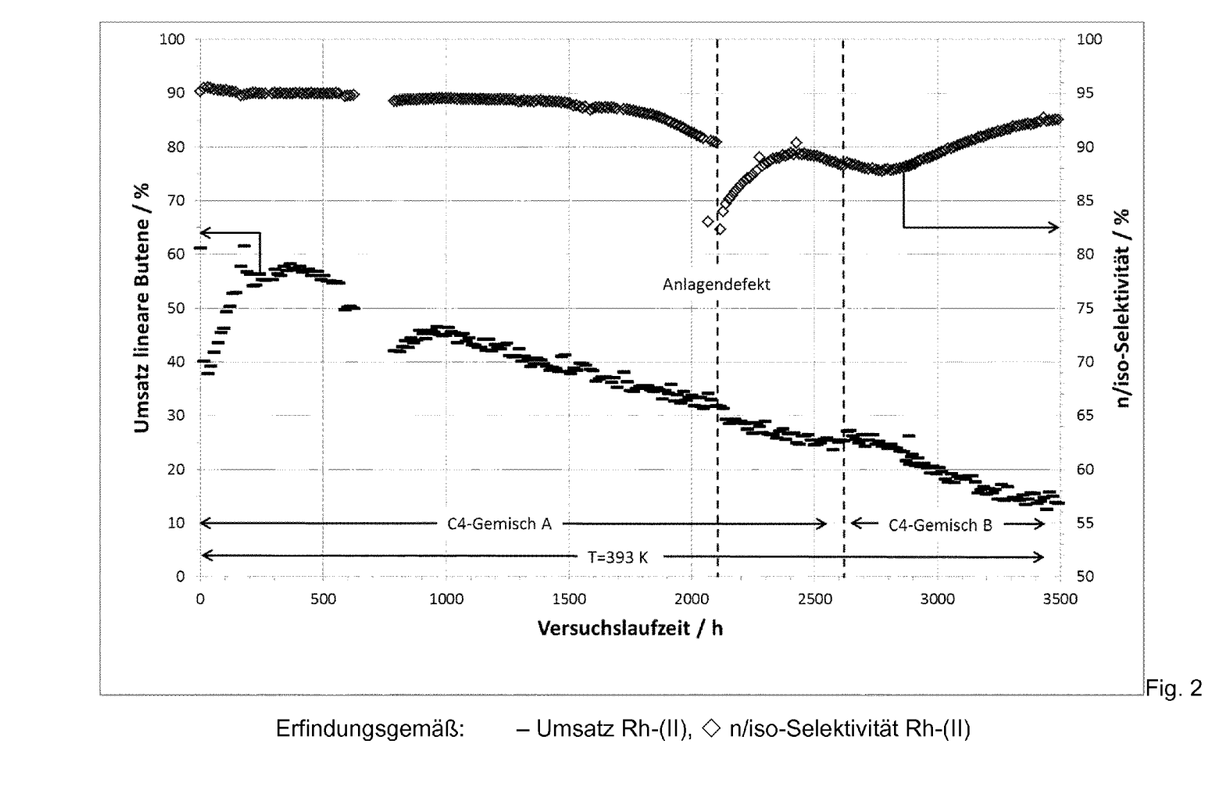
FIG. 2 shows a conversion/time diagram for C4 hydroformylation with Rh(II) catalysts (-) and the n/iso selectivity (◊). Parameters: m$_{cat}$=12 g, m$_{Rh}$=0.2% by wt., L/Rh=10, -, ◊: T=393.15 K; p=1 MPa; p(1- and 2-butenes)=0.16 MPa; p(butanes)=0.06 MPa; p(H$_2$)= p(CO)=0.39 MPa, H$_2$/1-butene ratio=6, residence time=58 s. For better clarity, only every 10th measurement found is shown. 2106 h: brief system shutdown because of a fault in the system without ingress of atmospheric oxygen.

The catalytically active Rh(II) composition of the invention, with the unsymmetrically substituted bisphosphite ligand (II), compared to Rh(III), exhibits a somewhat smaller n/iso selectivity averaging >90% (cf. FIG. 2) but a conversion of >55% after 500 h. This is astonishingly above the conversions achieved by Rh(III). Rh(II) likewise exhibits a distinctly prolonged service life of more than 3500 h. The reaction temperature was 120° C. over the entire onstream time of 3500 h. The reaction profile with the catalytically active Rh(II) composition shows only a creeping decline in conversion and no drop in the conversion, as shown in FIG. 1 with the Rh(III) system. Even after a fault in the plant without ingress of atmospheric oxygen at 2106 h, the n/iso selectivity of the catalytically active Rh(II) composition recovers again from <83% to >90%.

This result is surprising, since unsymmetric substituted bisphosphites show distinct losses of selectivity compared to symmetrically substituted examples, as already stated in Rhodium-catalyzed Hydroformylation, ed. by P. W. N. M. van Leeuwen and C. Claver, Kluwer Academic Publishers 2006, AA Dordrecht, NL, pages 45-46. In addition, the Rh(II) composition of the invention is found to be much more thermally stable than Rh(III).

Moreover, the long-term stability of ligand (II) indicates better stability of (II) with respect to water. The higher reaction temperature of the catalytically active Rh(II) composition should result in an increase in the likewise thermally induced aldol condensation compared to the catalysis results for Rh(III) in the experimental period of 0 h to 829 h.

Ligand (II) in the catalytically active composition thus firstly features a much better long-term stability than all the ligands described in the prior art to date, and secondly the additional capability of isomerizing hydroformylation combined with good n/iso selectivities, and hence achieves the stated object. Optimal long-term stability of the catalytically active composition is of significance especially in industrial scale application, since the heterogenization of the catalysis process, by contrast with the hydroformylation conducted in a homogeneous phase, does not enable replenishment of this composition and components thereof.

The invention claimed is:

1. A composition comprising:
   a) at least one support material which is porous;
   b) at least one metal selected from transition group VIII of the Periodic Table of the Elements;
   c) at least one compound of the formula (II)

(II)

2. The composition as claimed in claim 1, wherein the porous support material has the following surface parameters:
   i) mean pore diameter within a range from 1 to 423 nm;
   ii) pore volume within a range from 0.1 to 2 mL/g;
   iii) BET surface area within a range from 10 to 2050 m²/g.

3. The composition as claimed in claim 1, wherein the porous support material includes oxides of silicon, of aluminum, of titanium or of zirconium or activated carbon, or consists of mixtures thereof.

4. The composition as claimed in claim 1, wherein the metal is selected from cobalt, rhodium, iridium, ruthenium.

5. The composition as claimed in claim 4, wherein the metal is rhodium.

6. A process for producing a composition as claimed in claim 1, having the steps of:
   A) initially charging a precursor of at least one compound of a metal from transition group VIII of the Periodic Table of the Elements;
   B) contacting at least one compound of a metal from transition group VIII of the Periodic Table of the Elements with a molar excess of at least one organic phosphorus compound of the formula (II)

(II)

using an inert solvent;
   C) adding at least one porous inert support material to the mixture generated in B);
   D) removing the inert solvent to obtain the composition.

7. A process for hydroformylating unsaturated compounds, characterized in that a composition as claimed in claim 1 is used as catalyst.

8. The process as claimed in claim 7, characterized in that a fixed bed reactor containing the composition is used.

9. The process as claimed in claim 7, characterized in that the unsaturated compounds are selected from $C_2$-$C_4$ olefins and the industrial mixtures thereof.

10. The process as claimed in claim 9, characterized in that the unsaturated compounds are selected from ethene, propene, butenes and the industrial mixtures thereof.

* * * * *